United States Patent
Nirogi et al.

(10) Patent No.: US 10,603,323 B2
(45) Date of Patent: Mar. 31, 2020

(54) COMBINATION OF HISTAMINE-3 RECEPTOR INVERSE AGONISTS WITH ACETYLCHOLINESTERASE INHIBITORS

(71) Applicant: SUVEN LIFE SCIENCES LIMITED, Banjara Hills, Hyderabad, Telangana (IN)

(72) Inventors: Ramakrishna Nirogi, Telangana (IN); Anil Karbhari Shinde, Telangana (IN); Abdul Rasheed Mohammed, Telangana (IN); Pradeep Jayarajan, Telangana (IN); Gopinadh Bhyrapuneni, Talangana (IN); Venkateswarlu Jasti, Telangana (IN)

(*) Notice: Subject to any disclaimer, the term of this patent is extended or adjusted under 35 U.S.C. 154(b) by 0 days.

(21) Appl. No.: 16/320,949

(22) PCT Filed: Aug. 14, 2017

(86) PCT No.: PCT/IB2017/054938
§ 371 (c)(1),
(2) Date: Jan. 25, 2019

(87) PCT Pub. No.: WO2018/033847
PCT Pub. Date: Feb. 22, 2018

(65) Prior Publication Data
US 2019/0160075 A1    May 30, 2019

(30) Foreign Application Priority Data
Aug. 18, 2016 (IN) .............................. 201641028166

(51) Int. Cl.
*A61K 31/535* (2006.01)
*A61K 31/55* (2006.01)
(Continued)

(52) U.S. Cl.
CPC .......... *A61K 31/5377* (2013.01); *A61K 31/27* (2013.01); *A61K 31/445* (2013.01); *A61K 31/55* (2013.01); *A61P 25/28* (2018.01)

(58) Field of Classification Search
CPC .. A61K 31/5377; A61K 31/27; A61K 31/445; A61K 31/55
(Continued)

(56) References Cited

U.S. PATENT DOCUMENTS

| 9,079,888 B2 | 7/2015 | Nirogi | |
| 2012/0077802 A1* | 3/2012 | Chytil | C07D 491/10 514/212.02 |

(Continued)

FOREIGN PATENT DOCUMENTS

| WO | 2014/136075 | 9/2014 |
| WO | 2015/032966 | 3/2015 |

OTHER PUBLICATIONS

Brioni et al. "Discovery of Histamine H3 Antagonist for the Treatment of Cognitive Disorders and Alzhenner's Disease" The Journal of Pharmacology and Experimental Therapeutics, 2011, vol. 36, No. 1, pp. 38-46. (Year: 2011).*
(Continued)

*Primary Examiner* — Shengjun Wang
(74) *Attorney, Agent, or Firm* — IpHorgan Ltd.

(57) ABSTRACT

The present invention relates to the combination of histamine-3 receptor inverse agonist and acetylcholinesterase inhibitor. Also, the present invention provides histamine-3 receptor ($H_3R$) inverse agonist, or the pharmaceutically acceptable salt(s) thereof in combination with or as adjunct to acetylcholinesterase inhibitor and their use in the treatment of cognitive disorders. The present invention further provides the pharmaceutical composition containing the said combination.

26 Claims, 7 Drawing Sheets

Data represents Mean ± SEM of Exploration Time (*$p<0.05$ Vs familiar object, Students paired 't' test), n=8-10.

Data represents Mean ± SEM of Exploration Time (***$p<0.001$ vs familiar object, Students paired 't' test), n=7-10.

(51) Int. Cl.
- A61K 31/445 (2006.01)
- A61K 31/27 (2006.01)
- A61K 31/5377 (2006.01)
- A61P 25/28 (2006.01)

(58) Field of Classification Search
USPC .............................. 514/235.5, 319, 479, 215
See application file for complete search history.

(56) References Cited

U.S. PATENT DOCUMENTS

2014/0135304 A1    5/2014   Nirogi
2015/0080379 A1    3/2015   Trocme-Thibierge

OTHER PUBLICATIONS

Baker, "Antagonist affinity measurement at the Gi-coupled human histamine H3 receptor expressed in CHO cells" BMC Pharmacol. 8:9 (2008); pp. 1-15. DOI 10.1186/1471-2210-8-9.

Birks, "Cholinesterase inhibitors for Alzheimer's disease (Review)" Cochrane Database of Systematic Reviews Issue 1 Article No. CD005593 (2006)—107 pages, total pdf.

Ennaceur and Delacour, "A new one-trial test for neurobiological studies of memory in rats. 1: Behavioral data" Behav Brain Res 31:47-59 (1998).

Esbenshade et al., "The histamine H3 receptor: an attractive target for the treatment of cognitive disorders" Br J Pharmacol 154:1166-1181 (2008).

Gbahou et al, "Protean agonism at histamine H3 receptors in vitro and in vivo" PNAS 100(19):11086-11091 (2003).

Hajos et al., "Modulation of Hippocampal Theta Oscillation by Histamine H3 Receptors" J. Pharmacol. Exper. Therap. 324(1):391-398 (2008).

Kenakin, "Principles: Receptor theory in pharmacology" Trends in Pharmacol. Sci 25(4):186-192 (2004).

Khan et al., "The dual-acting H3 receptor antagonist and AchE inhibitor UW-MD-71 dose-dependently enhances memory retrieval and reverses dizocilpine-induced memory impairment in rats" Behav. Brain Res. 297:155-164 (2016), available online Oct. 20, 2015, ISSN:0166-4328.

Laitinen et al., "Guanosine 5'-(γ-[35S]Thio)triphosphate Autoradiography Allows Selective Detection of Histamine H3 Receptor Dependent G Protein Activation in Rat Brain Tissue Sections" J Neurochem 71:808-816 (1998).

Morisset et al., "High constitutive activity of native H3 receptors regulates histamine neurons in brain" Nature 408:860-864 (2000).

Thompson et al., "The benefits and risks associated with cholinesterase inhibitor therapy in Alzheimer's disease" Exp Opin Drug Safety 3(5):425-440 (2004).

European Patent Office, "International Search Report" dated Nov. 3, 2017 in PCT Application No. PCT/IB2017/054938.

European Patent Office, "Written Opinion" dated Nov. 3, 2017 in PCT Application No. PCT/IB2017/054938.

European Patent Office, "International Preliminary Report on Patentability" completed Jul. 18, 2018 in PCT Application No. PCT/IB2017/054938, and "Response to Written Opinion" submitted by Applicant in PCT Application No. PCT/IB2017/054938 and dated Mar. 16, 2018.

* cited by examiner

Figure 1a:

Data represents Mean ± SEM of Exploration Time (*$p<0.05$ Vs familiar object, Students paired 't' test), n=8-10.

Figure 1b:

Data represents Mean ± SEM of Exploration Time (***$p<0.001$ vs familiar object, Students paired 't' test), n=7-10.

Figure 1c:

Data represents Mean ± SEM of Exploration Time, (**p<0.01 vs familiar object, Students paired 't' test), n=9-12

Figure 2:

Data represents Mean ± SEM of Exploration Time, (**p<0.01 vs familiar object, Students paired 't' test), n=9-11.

(a) Data expressed as Mean ± SEM. *$p<0.05$ and *$p<0.001$ Vs Donepezil alone (Bonferroni's post test) (b) Area under the curve (AUC) ± S.E.M. *$p<0.001$ Vs Donepezil alone (Unpaired "t" Test).

(a) Data expressed as Mean ± SEM. **$p<0.01$ Vs rivastigmine alone (Bonferroni's posttest)

(b) Area under the curve (AUC) ± S.E.M.

(a) Data expressed as Mean ± SEM. $*p<0.05$, $p<0.01$ and $*p<0.001$ Vs Donepezil alone (Bonferroni post test) (b) Area under the curve (AUC) ± S.E.M. $***p<0.001$ Vs Donepezil alone (Unpaired "t" Test).

(a) Data expressed as Mean ± SEM. **$p<0.01$ Vs Donepezil alone (Bonferroni post test).
(b) Area under the curve (AUC) ± S.E.M. *$p<0.05$ Vs Donepezil alone (Unpaired "t" Test).

(a) Data expressed as Mean ± S.E.M. *$p<0.05$, $p<0.01$ Vs Donepezil alone (Bonferroni's posttest) (b) Area under the curve value ± S.E.M. $p<0.01$ Vs Donepezil alone (unpaired "t" test).

COMBINATION OF HISTAMINE-3 RECEPTOR INVERSE AGONISTS WITH ACETYLCHOLINESTERASE INHIBITORS

CROSS REFERENCE TO RELATED APPLICATIONS

This application is a national stage completion application of PCT Application No. PCT/IB2017/054938, filed Aug. 14, 2017, and claims priority from India Application No. 201641028166, filed Aug. 18, 2016. Each of these applications is incorporated by reference herein in its entirety.

FIELD OF THE INVENTION

The present invention relates to histamine-3 receptor ($H_3R$) inverse agonists or the pharmaceutically acceptable salt(s) thereof in combination with or as adjunct to acetylcholinesterase inhibitors. The present invention further relates to the use of the combination and the pharmaceutical composition containing the said combination in the treatment of cognitive disorders.

BACKGROUND OF INVENTION

Alzheimer's disease (AD) is the most common cause of dementia worldwide. The exponential rise in the number of cases of AD in the past and the future projections over next few decades is anticipated to result in great pressure on the social and health-care systems of developed and developing economies alike. AD also imposes tremendous emotional and financial burden to the patient's family and community.

The current list of approved cognition enhancing drugs for AD is not long and historically been focused on acetylcholinesterase inhibitors (donepezil, rivastigmine and galantamine). These drugs act by inhibiting the hydrolysis of acetylcholine (ACh) into acetate and choline by targeting acetylcholinesterase (AChE) enzyme. Increasing the ACh levels in the synapse can stimulate cholinergic receptors and promote memory function. Although acetylcholinesterase inhibitors (AChEIs) can temporarily delay the progression of cognitive decline in AD, their effects are modest. ACh being present both in the central and peripheral nervous system, AChEIs produce several undesirable side effects such as gastrointestinal disturbances, bradycardia and excessive salivation that are associated with an action on peripheral muscarinic cholinergic receptors (*Expert Opinion on Drug Safety*, 3, 2004, 425-440). The limitation of AChE inhibitor class of drugs is that they are poorly tolerated, their efficacy is not sustained and they require constant dose-titration as the disease progresses (*Cochrane Database Systematic Reviews*, 2006, CD005593) which lead to significant patient noncompliance. The incidence and the severity of these side effects increase with the dose amount and in general more pronounced at the initiation of the treatment or after dose increase. Hence there is an unmet need of alternate therapy for treating cognition disorders.

The $H_3R$ is a G protein-coupled receptor (GPCR), mainly expressed in the anterior part of the cortex, hippocampus and the striatum. $H_3Rs$ function as both autoreceptors and heteroreceptors. It modulates the synthesis and release of several neurotransmitters which play an important role in cognition, mood and sensory gating. Preliminary literature reports suggest that $H_3R$ antagonists/inverse agonist may have promising utility for the treatment of various CNS disorders including AD, schizophrenia, attention-deficit hyperactivity disorder (ADHD), epilepsy, narcolepsy, neuropathic pain and metabolic disorders. Antagonism of this receptor by several investigational compounds has been shown to improve learning and memory in animal models.

The patent applications, WO2015032966, WO2014136075 and US20150080379 disclose the combination of $H_3R$ antagonist and acetylcholinesterase inhibitors for the treatment of AD. However, none of these combinations are approved for the treatment of AD. As the treatment of AD is chronic in nature, there is a desperate unmet medical need for better and safer treatment options. The current approved treatment for AD includes use of AChEI or NMDA antagonist alone or the combination of AChEI and NMDA antagonist. However, there remains the need for the new drugs/combination to treat the patients with AD. A therapeutic strategy eagerly sought for AD patients is to target an improvement with an adjunct to existing therapies that would bring additional relief for patients, lower the burden on the caregiver and allow the patient to enjoy a better quality of life without the need for institutional care and/or hospitalization.

Since the cause and development of the dementia depend on the different mechanisms, it may be an advantageous to use the combination of drugs working in different mechanism for the treatment of AD. This may in turn help to reduce side effects with better patient compliance and thus can be administered over a long period.

The compounds of the present invention are $H_3R$ inverse agonists with high affinity and very high selectivity over closely related receptor subtypes and improve learning and memory in animals. The $H_3R$ inverse agonist compounds mentioned here are described in U.S. Pat. No. 9,079,888B2 which is incorporated by reference. The preparation of these compounds is given in the said patent.

The instant invention provides $H_3R$ inverse agonist or the pharmaceutically acceptable salt(s) thereof, which may enhance the cognitive function of patients on treatment with acetylcholinesterase inhibitors. The present invention is based on the finding that the instant compounds with $H_3R$ inverse agonist affinity enhance and also prolong the effect of the acetylcholinesterase inhibitors. The combination of the instant invention demonstrates a synergistic effect in their pharmacological activity. Such combined administration of $H_3R$ inverse agonist and acetylcholinesterase inhibitor can result in beneficial effect to improve the therapeutic efficacy in humans.

SUMMARY OF THE INVENTION

The objective of the present invention is to provide an improved combination therapy for the treatment of cognitive disorders, such as Alzheimer's disease, schizophrenia, Parkinson's disease, lewy body dementia, vascular dementia, frontotemporal dementia, Down syndrome or Tourette's syndrome.

In the first aspect, the present invention relates to a combination of histamine-3 receptor inverse agonist and acetylcholinesterase inhibitor; wherein the histamine-3 receptor inverse agonist is selected from:

N-[4-(1-Cyclobutylpiperidin-4-yloxy)phenyl]-2-(morpholin-4-yl)acetamide;

N-[4-(1-Cyclopropylpiperidin-4-yloxy)phenyl]-2-(morpholin-4-yl)acetamide; and

N-[4-(1-Isopropylpiperidin-4-yloxy)phenyl]-2-(morpholin-4-yl)acetamide;

or a pharmaceutically acceptable salt thereof.

In another aspect, the present invention relates to a combination of histamine-3 receptor inverse agonist and acetylcholinesterase inhibitor; wherein the histamine-3 receptor inverse agonist is N-[4-(1-Cyclobutylpiperidin-4-yloxy)phenyl]-2-(morpholin-4-yl)acetamide or a pharmaceutically acceptable salt thereof.

In another aspect, the present invention relates to a combination of histamine-3 receptor inverse agonist and acetylcholinesterase inhibitor; wherein the histamine-3 receptor inverse agonist is N-[4-(1-Cyclopropylpiperidin-4-yloxy)phenyl]-2-(morpholin-4-yl)acetamide or a pharmaceutically acceptable salt thereof.

In another aspect, the present invention relates to a combination of histamine-3 receptor inverse agonist and acetylcholinesterase inhibitor; wherein the histamine-3 receptor inverse agonist is N-[4-(1-Isopropylpiperidin-4-yloxy)phenyl]-2-(morpholin-4-yl)acetamide or a pharmaceutically acceptable salt thereof.

In another aspect, the present invention relates to a combination of histamine-3 receptor inverse agonist and acetylcholinesterase inhibitor; wherein the acetylcholinesterase inhibitor is selected from donepezil, galantamine and rivastigmine or a pharmaceutically acceptable salt thereof.

In yet another aspect the present invention relates to a combination of N-[4-(1-Cyclobutylpiperidin-4-yloxy)phenyl]-2-(morpholin-4-yl)acetamide and donepezil or a pharmaceutically acceptable salt thereof.

In yet another aspect the present invention relates to the combination of N-[4-(1-Cyclopropylpiperidin-4-yloxy)phenyl]-2-(morpholin-4-yl)acetamide and donepezil or a pharmaceutically acceptable salt thereof.

In yet another aspect the present invention relates to the combination of N-[4-(1-Isopropylpiperidin-4-yloxy)phenyl]-2-(morpholin-4-yl)acetamide and donepezil or a pharmaceutically acceptable salt thereof.

In yet another aspect, the present invention relates to the said combination for use in the treatment of cognitive disorders.

In yet another aspect, the present invention relates to the said combination for use in the treatment of cognitive disorders such as Alzheimer's disease, schizophrenia, Parkinson's disease, lewy body dementia, vascular dementia, frontotemporal dementia, Down syndrome or Tourette's syndrome.

In yet another aspect, the present invention relates to a method of treatment of cognitive disorders such as Alzheimer's disease, schizophrenia, Parkinson's disease, lewy body dementia, vascular dementia, frontotemporal dementia, Down syndrome or Tourette' s syndrome comprising administering to a patient in need thereof a therapeutically effective amount of the said combination.

In yet another aspect, the present invention relates to histamine-3 receptor inverse agonist for use in the adjunct treatment of cognitive disorders such as Alzheimer's disease, schizophrenia, Parkinson's disease, lewy body dementia, vascular dementia, frontotemporal dementia, Down syndrome or Tourette's syndrome in patients on treatment with acetylcholinesterase inhibitor.

In yet another aspect, the present invention relates to the compound, N-[4-(1-Cyclobutylpiperidin-4-yloxy)phenyl]-2-(morpholin-4-yl)acetamide or a pharmaceutically acceptable salt thereof for use in the adjunct treatment of cognitive disorders such as Alzheimer's disease, schizophrenia, Parkinson's disease, lewy body dementia, vascular dementia, frontotemporal dementia, Down syndrome or Tourette's syndrome in patients on treatment with donepezil.

In yet another aspect, the present invention relates to the compound, N-[4-(1-Cyclobutylpiperidin-4-yloxy)phenyl]-2-(morpholin-4-yl)acetamide or a pharmaceutically acceptable salt thereof for use in combination with or adjunct to an acetylcholinesterase inhibitor for the treatment of cognitive disorders such as Alzheimer's disease, schizophrenia, Parkinson's disease, lewy body dementia, vascular dementia, frontotemporal dementia, Down syndrome or Tourette's syndrome.

In another aspect, the present invention relates to a method for treatment of cognitive disorders comprising administering to a patient in need thereof a therapeutically effective amount of N-[4-(1-Cyclobutylpiperidin-4-yloxy)phenyl]-2-(morpholin-4-yl)acetamide or a pharmaceutically acceptable salt thereof in combination with or as an adjunct to donepezil or a pharmaceutically acceptable salt thereof.

In yet another aspect, the present invention relates to use of a combination of histamine-3 receptor inverse agonist and acetylcholinesterase inhibitor for the treatment of cognitive disorders such as Alzheimer's disease, schizophrenia, Parkinson's disease, lewy body dementia, vascular dementia, frontotemporal dementia, Down syndrome or Tourette's syndrome.

In yet another aspect, the present invention relates to use of a combination of N-[4-(1-Cyclobutylpiperidin-4-yloxy)phenyl]-2-(morpholin-4-yl)acetamide and donepezil or a pharmaceutically acceptable salt thereof for the treatment of cognitive disorders such as Alzheimer's disease, schizophrenia, Parkinson's disease, lewy body dementia, vascular dementia, frontotemporal dementia, Down syndrome or Tourette's syndrome.

In another aspect, the present invention relates to pharmaceutical composition comprising the histamine-3 receptor inverse agonist and acetylcholinesterase inhibitor and pharmaceutically acceptable excipients or combination thereof.

In another aspect, the present invention relates to pharmaceutical composition comprising N-[4-(1-Cyclobutylpiperidin-4-yloxy)phenyl]-2-(morpholin-4-yl)acetamide and donepezil or a pharmaceutically acceptable salt thereof and the pharmaceutically acceptable excipients or combination thereof.

In another aspect, the present invention relates to pharmaceutical composition comprising the histamine-3 receptor inverse agonist and acetylcholinesterase inhibitor or a pharmaceutically acceptable salt thereof along with the pharmaceutically acceptable excipients or combination thereof for use in the treatment of cognitive disorders such as Alzheimer's disease, schizophrenia, Parkinson's disease, lewy body dementia, vascular dementia, frontotemporal dementia, Down syndrome or Tourette's syndrome.

BRIEF DESCRIPTION OF THE DIAGRAMS

DETAILED DESCRIPTION

Unless otherwise stated, the following terms used in the specification and claims have the meanings given below:

The term, "histamine-3 receptor inverse agonist" as used herein refers to a ligand or drug that binds with the constitutively active $H_3$ receptors, stabilize them, and thus reduce the activity (negative intrinsic activity). It blocks or inhibits the function/binding of agonist at the $H_3$ receptor and exert opposite pharmacological effect of a receptor agonist.

Examples of the histamine-3 receptor inverse agonist include, N-[4-(1-Cyclobutylpiperidin-4-yloxy)phenyl]-2-(morpholin-4-yl)acetamide; N-[4-(1-Cyclopropylpiperidin-4-yloxy)phenyl]-2-(morpholin-4-yl)acetamide; and N-[4-(1-Isopropylpiperidin-4-yloxy)phenyl]-2-(morpholin-4-yl) acetamide; or a pharmaceutically acceptable salt thereof.

Examples of pharmaceutically acceptable salt of the above identified compounds include but not limited to, N-[4-(1-Cyclobutylpiperidin-4-yloxy)phenyl]-2-(morpholin-4-yl)acetamide dihydrochloride; N-[4-(1-Cyclopropylpiperidin-4-yloxy)phenyl]-2-(morpholin-4-yl)acetamide tartrate; and N-[4-(1-Isopropylpiperidin-4-yloxy)phenyl]-2-(morpholin-4-yl)acetamide tartrate.

The term, "acetylcholinesterase inhibitor" as used herein is a chemical or drug that inhibits the acetylcholinesterase enzyme from breaking down acetylcholine, thereby increasing both the level and duration of action of the neurotransmitter acetylcholine. Examples of acetylcholinesterase inhibitor are donepezil, rivastigmine and galantamine. Preferably, the acetylcholinesterase inhibitor is donepezil and rivastigmine. More preferably the acetylcholinesterase inhibitor is donepezil.

Donepezil is a drug approved for treatment of mild, moderate and severe dementia of Alzheimer's disease. Donepezil is a reversible inhibitor of the enzyme acetylcholinesterase and sold under trade name Aricept® as hydrochloride salt.

Rivastigmine is a drug approved for treatment of mild, moderate and severe dementia of Alzheimer's disease. Rivastigmine is a reversible cholinesterase inhibitor and sold under trade name Exelon® and Exelon Patch® as tartrate salt.

Galantamine is a drug approved for treatment of mild, moderate and severe dementia of Alzheimer' s disease. Galantamine, a reversible, competitive acetylcholinesterase inhibitor and sold under trade name Razadyne® as hydrobromide salt.

The phrase, "therapeutically effective amount" is defined as an amount of a compound of the present invention that (i) treats the particular disease, condition or disorder, (ii) eliminates one or more symptoms of the particular disease, condition or disorder and (iii) delays the onset of one or more symptoms of the particular disease, condition or disorder described herein.

The term, "pharmaceutically acceptable salt" as used herein refers to salts of the active compound and are prepared by reaction with the appropriate organic or inorganic acid or acid derivative, depending on the particular substituents found on the compounds described herein.

The term, "patient" as used herein refers to an animal. Preferably the term "patient" refers to mammal. The term mammal includes animals such as mice, rats, dogs, rabbits, pigs, monkeys, horses and human. More preferably the patient is human.

The term, "Alzheimer's disease" as used herein refers to a dementia that causes problems with memory, thinking and behavior. The Alzheimer's disease can be mild to moderate to severe Alzheimer's disease.

The compound 1 as used herein is N-[4-(1-Cyclobutylpiperidin-4-yloxy)phenyl]-2-(morpholin-4-yl)acetamide dihydrochloride which has the chemical structure, The compound 2 as used herein is N-[4-(1-Cyclopropylpiperidin-4-yloxy)phenyl]-2-(morpholin-4-yl)acetamide tartrate which has the chemical structure, The compound 3 as used herein is N-[4-(1-Isopropylpiperidin-4-yloxy)phenyl]-2-(morpholin-4-yl)acetamide which has the chemical structure, The term, "treatment' or 'treating" as used herein refers to any treatment of a disease in a mammal, including: (a) slowing or arresting the development of clinical symptoms; and/or (b) causing the regression of clinical symptoms.

The term, "compound for use" as used herein embrace any one or more of the following: (1) use of a compound, (2) method of use of a compound, (3) use in the treatment of, (4) the use for the manufacture of pharmaceutical composition/medicament for treatment/treating or (5) method of treatment/treating/preventing/reducing/inhibiting comprising administering an effective amount of the active compound to a subject in need thereof.

The term, "cognitive disorder" as used herein refers to a group of mental health disorders that principally affect learning, memory, perception and problem solving and includes amnesia, dementia and delirium. Cognitive disorders can result due to disease, disorder, ailment or toxicity. Example of cognitive disorders includes but not limited to, Alzheimer's disease, schizophrenia, Parkinson's disease, lewy body dementia (LBD), vascular dementia, frontotemporal dementia (FTD), Down syndrome or Tourette's syndrome. Preferably, the cognitive disorder is Alzheimer's disease.

The term, "adjunct" or "adjunctive treatment" as used herein refers to an additional treatment to a patient who has already received at least one other therapy for cognitive disorders. A drug used as adjunctive therapy is administered to a patient to make that primary treatment works better.

Embodiments

The present invention encompasses all the combinations described herein without limitation, however, preferred aspects and elements of the invention are discussed herein in the form of the following embodiments.

In one embodiment, the present invention relates to the combination of histamine-3 receptor inverse agonist and acetylcholinesterase inhibitor; wherein the histamine-3 receptor inverse agonist is N-[4-(1-Cyclobutylpiperidin-4-yloxy)phenyl]-2-(morpholin-4-yl)acetamide dihydrochloride.

In another embodiment, the present invention relates to the combination of histamine-3 receptor inverse agonist and acetylcholinesterase inhibitor; wherein the histamine-3 receptor inverse agonist is N-[4-(1-Cyclopropylpiperidin-4-yloxy)phenyl]-2-(morpholin-4-yl)acetamide tartrate.

In another embodiment, the present invention relates to the combination of histamine-3 receptor inverse agonist and acetylcholinesterase inhibitor; wherein the histamine-3 receptor inverse agonist is N-[4-(1-Isopropylpiperidin-4-yloxy)phenyl]-2-(morpholin-4-yl)acetamide tartrate.

In another embodiment, the present invention relates to the combination of N-[4-(1-Cyclobutylpiperidin-4-yloxy)phenyl]-2-(morpholin-4-yl)acetamide and rivastigmine or a pharmaceutically acceptable salt thereof.

In another embodiment, the present invention relates to the combination of N-[4-(1-Cyclobutylpiperidin-4-yloxy)phenyl]-2-(morpholin-4-yl)acetamide and galantamine or a pharmaceutically acceptable salt thereof.

In another embodiment, the present invention relates to the combination of N-[4-(1-Cyclopropylpiperidin-4-yloxy)phenyl]-2-(morpholin-4-yl)acetamide and rivastigmine or a pharmaceutically acceptable salt thereof.

In another embodiment, the present invention relates to the combination of N-[4-(1-Cyclopropylpiperidin-4-yloxy)phenyl]-2-(morpholin-4-yl)acetamide and galantamine or a pharmaceutically acceptable salt thereof.

In another embodiment, the present invention relates to the combination of N-[4-(1-Isopropylpiperidin-4-yloxy)phenyl]-2-(morpholin-4-yl)acetamide and rivastigmine or a pharmaceutically acceptable salt thereof.

In another embodiment, the present invention relates to the combination of N-[4-(1-Isopropylpiperidin-4-yloxy)phenyl]-2-(morpholin-4-yl)acetamide and galantamine or a pharmaceutically acceptable salt thereof.

In another embodiment, the present invention relates to the combination of N-[4-(1-Cyclobutylpiperidin-4-yloxy)phenyl]-2-(morpholin-4-yl)acetamide dihydrochloride and donepezil hydrochloride.

In another embodiment, the present invention relates to the combination of N-[4-(1-Cyclobutylpiperidin-4-yloxy)phenyl]-2-(morpholin-4-yl)acetamide dihydrochloride and rivastigmine tartrate.

In another embodiment, the present invention relates to the combination of N-[4-(1-Cyclobutylpiperidin-4-yloxy)phenyl]-2-(morpholin-4-yl)acetamide dihydrochloride and galantamine hydrobromide.

In another embodiment, the present invention relates to the combination of N-[4-(1-Cyclopropylpiperidin-4-yloxy)phenyl]-2-(morpholin-4-yl)acetamide tartrate and donepezil hydrochloride.

In another embodiment, the present invention relates to the combination of N-[4-(1-Cyclopropylpiperidin-4-yloxy)phenyl]-2-(morpholin-4-yl)acetamide tartrate and rivastigmine tartrate.

In another embodiment, the present invention relates to the combination of N-[4-(1-Cyclopropylpiperidin-4-yloxy)phenyl]-2-(morpholin-4-yl)acetamide tartrate and galantamine hydrobromide.

In another embodiment, the present invention relates to the combination of N-[4-(1-Isopropylpiperidin-4-yloxy)phenyl]-2-(morpholin-4-yl)acetamide tartrate and donepezil hydrochloride.

In another embodiment, the present invention relates to the combination of N-[4-(1-Isopropylpiperidin-4-yloxy)phenyl]-2-(morpholin-4-yl)acetamide tartrate and rivastigmine tartrate.

In another embodiment, the present invention relates to the combination of N-[4-(1-Isopropylpiperidin-4-yloxy)phenyl]-2-(morpholin-4-yl)acetamide tartrate and galantamine hydrobromide.

In another embodiment, the present invention provides the combination of the histamine-3 receptor inverse agonist and acetylcholinesterase inhibitor which is more effective than the histamine-3 receptor inverse agonist and acetylcholinesterase inhibitor alone.

In another embodiment, the present invention provides the combination of N-[4-(1-Cyclobutylpiperidin-4-yloxy)phenyl]-2-(morpholin-4-yl)acetamide dihydrochloride and donepezil hydrochloride which is more effective than N-[4-(1-Cyclobutylpiperidin-4-yloxy)phenyl]-2-(morpholin-4-yl)acetamide dihydrochloride and donepezil hydrochloride alone.

In another embodiment the pharmaceutically acceptable salt of histamine-3 receptor inverse agonist includes but not limited to, dihydrochloride salt, oxalate salt, succinate salt, tartrate salt and the like. Preferably, the pharmaceutically acceptable salt is dihydrochloride salt and tartrate salts. More preferably, the pharmaceutically acceptable salt is dihydrochloride salt.

In another embodiment, the present invention relates to a method of treating Alzheimer's disease comprising administering to a patient in need thereof a therapeutically effective amount of the said combination.

In another embodiment, the present invention relates to a method of treating Alzheimer's disease comprising administering to a patient in need thereof a therapeutically effective amount of N-[4-(1-Cyclobutylpiperidin-4-yloxy)phenyl]-2-(morpholin-4-yl)acetamide or a pharmaceutically acceptable salt thereof and acetylcholinesterase inhibitor.

In another embodiment, the present invention relates to a method of treating Alzheimer's disease comprising administering to a patient in need thereof a therapeutically effective amount of N-[4-(1-Cyclopropylpiperidin-4-yloxy)phenyl]-2-(morpholin-4-yl)acetamide or a pharmaceutically acceptable salt thereof and acetylcholinesterase inhibitor.

In another embodiment, the present invention relates to a method of treating Alzheimer's disease comprising administering to a patient in need thereof a therapeutically effective amount of N-[4-(1-Isopropylpiperidin-4-yloxy)phenyl]-2-(morpholin-4-yl)acetamide or a pharmaceutically acceptable salt thereof and acetylcholinesterase inhibitor.

In another embodiment, the present invention relates to a method of treating Alzheimer's disease comprising administering to a patient in need thereof a therapeutically effective amount of N-[4-(1-Cyclobutylpiperidin-4-yloxy)phenyl]-2-(morpholin-4-yl)acetamide or a pharmaceutically acceptable salt thereof in combination with acetylcholinesterase inhibitor.

In another embodiment, the present invention relates to a method of treating Alzheimer's disease comprising administering to a patient in need thereof a therapeutically effective amount of N-[4-(1-Cyclopropylpiperidin-4-yloxy)phenyl]-2-(morpholin-4-yl)acetamide or a pharmaceutically acceptable salt thereof in combination with acetylcholinesterase inhibitor.

In another embodiment, the present invention relates to a method of treating Alzheimer's disease comprising administering to a patient in need thereof a therapeutically effective amount of N-[4-(1-Isopropylpiperidin-4-yloxy)phenyl]-2-(morpholin-4-yl)acetamide or a pharmaceutically acceptable salt thereof in combination with acetylcholinesterase inhibitor.

In another embodiment, the present invention relates to a method of treating Alzheimer's disease comprising administering to a patient in need thereof a therapeutically effective amount of N-[4-(1-Cyclobutylpiperidin-4-yloxy)phenyl]-2-(morpholin-4-yl)acetamide dihydrochloride in combination with acetylcholinesterase inhibitor.

In another embodiment, the present invention relates to a method of treating Alzheimer's disease comprising administering to a patient in need thereof a therapeutically effective amount of N-[4-(1-Cyclopropylpiperidin-4-yloxy)phenyl]-2-(morpholin-4-yl)acetamide tartrate in combination with acetylcholinesterase inhibitor.

In another embodiment, the present invention relates to a method of treating Alzheimer's disease comprising administering to a patient in need thereof a therapeutically effective amount of N-[4-(1-Isopropylpiperidin-4-yloxy)phenyl]-2-(morpholin-4-yl)acetamide tartrate in combination with acetylcholinesterase inhibitor.

In another embodiment, the present invention relates to a method of treating Alzheimer's disease comprising administering to a patient in need thereof a therapeutically effective amount of N-[4-(1-Cyclobutylpiperidin-4-yloxy)phenyl]-2-(morpholin-4-yl)acetamide dihydrochloride in combination with donepezil or a pharmaceutically acceptable salt thereof.

In another embodiment, the present invention relates to a method of treating Alzheimer's disease comprising administering to a patient in need thereof a therapeutically effective amount of N-[4-(1-Cyclobutylpiperidin-4-yloxy)phenyl]-2-(morpholin-4-yl)acetamide dihydrochloride in combination with donepezil hydrochloride.

In another embodiment, the present invention relates to the combination of N-[4-(1-Cyclobutylpiperidin-4-yloxy)phenyl]-2-(morpholin-4-yl)acetamide dihydrochloride and acetylcholinesterase inhibitor for use in the treatment of Alzheimer's disease.

In yet another aspect, the present invention relates to N-[4-(1-Cyclobutylpiperidin-4-yloxy)phenyl]-1-2-(morpholin-4-yl)acetamide or a pharmaceutically acceptable salt thereof for use in the adjunct treatment of Alzheimer's disease in a patient on treatment with acetylcholinesterase inhibitor.

In yet another aspect, the present invention relates to N-[4-(1-Cyclopropylpiperidin-4-yloxy)phenyl]-2-(morpholin-4-yl)acetamide or a pharmaceutically acceptable salt thereof for use in the adjunct treatment of Alzheimer's disease in a patient on treatment with acetylcholinesterase inhibitor.

In yet another aspect, the present invention relates to N-[4-(1-Isopropylpiperidin-4-yloxy)phenyl]-2-(morpholin-4-yl)acetamide or a pharmaceutically acceptable salt thereof for use in the adjunct treatment of Alzheimer's disease in a patient on treatment with acetylcholinesterase inhibitor.

In another embodiment, the present invention relates to N-[4-(1-Cyclobutylpiperidin-4-yloxy)phenyl]-2-(morpholin-4-yl)acetamide dihydrochloride for use in the adjunct treatment of Alzheimer's disease in a patient on treatment with donepezil or a pharmaceutically acceptable salt thereof.

In another embodiment, the present invention relates to N-[4-(1-Cyclopropylpiperidin-4-yloxy)phenyl]-2-(morpholin-4-yl)acetamide tartrate for use in the adjunct treatment of Alzheimer's disease in a patient on treatment with donepezil or a pharmaceutically acceptable salt thereof.

In another embodiment, the present invention relates to N-[4-(1-Isopropylpiperidin-4-yloxy)phenyl]-2-(morpholin-4-yl)acetamide tartrate for use in the adjunct treatment of Alzheimer's disease in a patient on treatment with donepezil or a pharmaceutically acceptable salt thereof.

In another embodiment, the present invention relates to use of the combination of histamine-3 receptor inverse agonist and acetylcholinesterase inhibitor in the manufacture of a medicament for the treatment of cognitive disorders.

In another embodiment, the present invention relates to use of the combination of histamine-3 receptor inverse agonist and acetylcholinesterase inhibitor in the manufacture of a medicament for the treatment of cognitive disorders selected from Alzheimer's disease, schizophrenia, Parkinson's disease, lewy body dementia, vascular dementia, frontotemporal dementia, Down syndrome or Tourette' s syndrome.

In another embodiment, the present invention relates to use of the combination of histamine-3 receptor inverse agonist and acetylcholinesterase inhibitor in the manufacture of a medicament for treatment of Alzheimer's disease.

In another embodiment, the present invention relates to use of histamine-3 receptor inverse agonist in the manufacture of a medicament for treatment of Alzheimer's disease in combination with acetylcholinesterase inhibitor.

In another embodiment, the present invention relates to use of histamine-3 receptor inverse agonist in the manufacture of a medicament for treatment of Alzheimer' s disease as adjunct to acetylcholinesterase inhibitor.

In another embodiment, the present invention relates to use of the N-[4-(1-Cyclobutylpiperidin-4-yloxy)phenyl]-2-(morpholin-4-yl)acetamide or a pharmaceutically acceptable salt thereof in the manufacture of a medicament for the treatment of Alzheimer's disease in combination with donepezil or a pharmaceutically acceptable salt thereof.

In another embodiment, the present invention relates to use of the N-[4-(1-Cyclobutylpiperidin-4-yloxy)phenyl]-2-(morpholin-4-yl)acetamide dihydrochloride in the manufacture of a medicament for treatment of Alzheimer's disease in combination with donepezil or a pharmaceutically acceptable salt thereof.

In another embodiment, the present invention relates to use of N-[4-(1-Cyclobutylpiperidin-4-yloxy)phenyl]-2-(morpholin-4-yl)acetamide dihydrochloride in the manufacture of a medicament for treatment of Alzheimer's disease in combination with donepezil hydrochloride.

In another embodiment, the present invention relates to the combination for treatment of Alzheimer's disease, wherein Alzheimer's disease is mild Alzheimer's disease.

In another embodiment, the present invention relates to the combination for treatment of Alzheimer's disease, wherein the Alzheimer's disease is moderate Alzheimer's disease.

In another embodiment, the present invention relates to the combination for treatment of Alzheimer's disease, wherein the Alzheimer's disease is severe Alzheimer's disease.

In another embodiment, the present invention relates to the combination wherein the active ingredients can be administered to a patient concurrently or separately.

In yet another aspect, the active ingredients of the combination of the present invention are normally administered by formulating the active ingredients into a pharmaceutical composition in accordance with standard pharmaceutical practice.

In yet another aspect, the active ingredients of the combination of the present invention may be administered by oral, nasal, local, dermal or parenteral routes.

In yet another aspect, the active ingredients of the combination of the present invention can be administered by the same or different route of administration. For instance, the histamine-3 receptor inverse agonist of the instant invention can be administered orally and the acetylcholinesterase inhibitor can be administered transdermally.

The pharmaceutical compositions of the present invention may be formulated in a conventional manner using one or more pharmaceutically acceptable excipients. The pharmaceutically acceptable excipients are diluents, disintegrants, binders, lubricants, glidants, polymers, coating agents, solvents, co-solvents, preservatives, wetting agents, thickening agents, antifoaming agents, sweetening agents, flavouring agents, antioxidants, colorants, solubilizers, plasticizer, dispersing agents and the like. Excipients are selected from microcrystalline cellulose, mannitol, lactose, pregelatinized starch, sodium starch glycolate, corn starch or derivatives thereof, povidone, crospovidone, calcium stearate, glyceryl monostearate, glyceryl palmitostearate, talc, colloidal silicone dioxide, magnesium stearate, sodium lauryl sulfate, sodium stearyl fumarate, zinc stearate, stearic acid or hydrogenated vegetable oil, gum arabica, magnesia, glucose, fats, waxes, natural or hardened oils, water, physiological sodium chloride solution or alcohols, for example, ethanol, propanol or glycerol, sugar solutions, such as glucose solutions or mannitol solutions and the like or a mixture of the various excipients.

In yet another aspect, the active compounds of the invention may be formulated in the form of pills, tablets, coated tablets, capsules, powder, granules, pellets, patches, implants, films, liquids, semi-solids, gels, aerosols, emulsions, elixirs and the like. Such pharmaceutical compositions and processes for preparing same are well known in the art.

In yet another aspect, the pharmaceutical composition of the instant invention contains 1 to 90%, 5 to 75% and 10 to 60% by weight of the compounds of the instant invention or pharmaceutically acceptable salt thereof. The amount of the active compounds or its pharmaceutically acceptable salt in the pharmaceutical composition(s) can range from about 0.1 mg to about 100 mg or from about 0.1 mg to about 60 mg or from about 0.1 mg to about 30 mg or in any range falling within the broader range of 0.1 mg to 100 mg.

In yet another aspect, the pharmaceutical composition of the combination of the instant invention can be conventional formulations such as immediate release formulations, modified release formulations such as sustained release formulations, delayed release formulations and extended release formulations or new delivery systems such as oral disintegrating formulations and transdermal patches.

The dose of the active compounds can vary depending on factors such as age and weight of patient, nature, route of administration and severity of the disease to be treated and such other factors. Therefore, any reference regarding pharmacologically effective amount of the compounds 1, 2 and 3 refers to the aforementioned factors.

In yet another aspect, the histamine-3 receptor inverse agonist can be co-administered with acetylcholinesterase inhibitor at a daily dose of 0.1 mg to 100 mg; such as 0.1, 0.5, 0.75, 1, 1.5, 3, 5, 6, 10, 20, 25, 30, 50, 75 and 100 mg, preferably at a daily dose of 0.1, 3, 5, 6, 10, 20, 25, 30 or 50 mg and most preferably at a daily dose of 0.5, 3, 5, 10 or 20 mg.

In yet another aspect, the acetylcholinesterase inhibitor can be co-administered with histamine-3 receptor inverse agonist at a daily dose of 1 mg to 30 mg; such as 1, 1.5, 2, 3, 4, 4.5, 5, 6, 8, 9.5,10, 12, 13, 13.3, 15, 16, 23, 24, 25 or 30 mg, preferably at a daily dose of 1, 1.5, 2, 3, 4, 4.5, 5, 6, 8, 9.5, 10, 12, 13, 13.3, 16, 23, 24, or 25 mg and most preferably at a daily dose of 1.5, 3, 4, 4.5, 5, 6, 8, 9.5, 10, 12, 13.3, 16, 23 or 24 mg.

In yet another aspect, the acetylcholinesterase inhibitor, donepezil can be co-administered with histamine-3 receptor inverse agonist at a daily dose of 2 mg to 30 mg; such as 2, 5, 10, 15, 23, 25 or 30 mg, preferably at a daily dose of 2, 5, 10, 23 or 25 mg and most preferably at a daily dose of 5, 10 or 23 mg.

In yet another aspect, the acetylcholinesterase inhibitor, rivastigmine can be co-administered with histamine-3 receptor inverse agonist at a daily dose of 0.5 mg to 15 mg; such as 0.5, 1, 1.5, 3, 4.5, 5, 6, 9.5, 10, 13.3, 15 mg, preferably at a daily dose of 1, 1.5, 3, 4.5, 5, 6, 9.5 or 13.3 mg and most preferably at a daily dose of 1.5, 3, 4.5, 6, 9.5 and 13.3 mg.

In yet another aspect, the acetylcholinesterase inhibitor, galantamine can be co-administered with histamine-3 receptor inverse agonist at a daily dose of 1 mg to 30 mg; such as 1, 2, 4, 6, 8, 12, 16, 24 and 30 mg, preferably at a daily dose of 2, 4, 6, 8, 12, 16 and 24 mg and most preferably at a daily dose of 4, 8, 12, 16 and 24 mg.

In yet another aspect, the treatment comprises administering to the patient 0.1 mg to 100 mg of N-[4-(1-Cyclobutylpiperidin-4-yloxy)phenyl]-2-(morpholin-4-yl)acetamide or a pharmaceutically acceptable salt thereof, per day.

In yet another aspect, the treatment comprises administering to the patient 0.1 mg to 60 mg of N-[4-(1-Cyclobutylpiperidin-4-yloxy)phenyl]-2-(morpholin-4-yl)acetamide or a pharmaceutically acceptable salt thereof, per day.

In yet another aspect, the treatment comprises administering to the patient 0.1 mg to 30 mg of N-[4-(1-Cyclobutylpiperidin-4-yloxy)phenyl]-2-(morpholin-4-yl)acetamide or a pharmaceutically acceptable salt thereof, per day.

In yet another aspect, the treatment comprises administering to the patient 1 mg to 25 mg of donepezil or a pharmaceutically acceptable salt thereof, per day.

In yet another aspect, the treatment comprises administering to the patient 5 mg to 25 mg of donepezil or a pharmaceutically acceptable salt thereof, per day.

In yet another aspect, the treatment comprises administering to the patient, 5, 10 or 23 mg of donepezil or a pharmaceutically acceptable salt thereof, per day.

In yet another aspect, the treatment comprises administering the active compounds to the patient one to three times per day, one to three times per week or one to three times per month. Preferably, the treatment comprises administering the compound to a patient once a day, twice a day, or thrice a day. More preferably, the treatment comprises administering the compound to a patient once a day.

EXAMPLES

The examples given below are provided by the way of illustration only and therefore should not be construed to limit the scope of the invention.
Abbreviations:
ANOVA: Analysis of variance
AP: Anterior Posterior
aCSF: Artificial Cerebrospinal fluid
$CaCl_2 \cdot 2H_2O$: Calcium chloride dihydrate
DV: Dorsal Ventral
DTT: Dithiothreitol
$EC_{50}$: Half maximal effective concentration
EDTA: Ethylenediaminetetraacetic acid
EEG: Electroencephalogram
GDP: Guanosine diphosphate
GPCR: G-Protein Coupled Receptor
HCl: Hydrochloric acid
h: Hour (s)
HEPES: 4-(2-Hydroxyethyl)piperazine-1-ethanesulfonic acid
i.p.: Intraperitoneal
i.v.: Intravenous
KCl: Potassium chloride
$K_b$: Binding constant
$K_i$: Inhibitory constant
LC-MS/MS: Liquid chromatography-Mass spectrometry/Mass spectrometry
mg: Milligram
$MgCl_2$: Magnesium chloride
min: Minute (s)
ML: Medial Lateral
mM: Millimolar
nmol/L: Nanomoles per litre
NaCl: Sodium chloride
$NaH_2PO_4 \cdot 2H_2O$: Sodium dihydrogen phosphate dihydrate
$Na_2HPO_4 \cdot 7H_2O$: Sodium monohydrogen phosphate heptahydrate
NPO: Nucleus Pontis Oralis
nM: Nanomolar
p.o.: Per oral
s.c.: Subcutaneous
S.E.M. Standard error of the mean
µM: Micromolar
θ: Theta

Example 1

Determination of $K_i$ Value at Human and Rat Histamine-3 Receptor

Test compounds were evaluated according to the following procedures to determine the $K_i$ value at human and rat histamine-3 receptor.
Materials and Methods:
Receptor source: Rat brain frontal cortex or recombinant human cDNA expressed in CHO cells
Radioligand: [3H] R-α-methylhistamine
Final ligand concentration: [3.0 nM]
Non-specific determinant: R-α-methylhistamine (100 µM)
Reference compound: R-α-methylhistamine
Positive control: R-α-methylhistamine
Incubation Conditions:

Increasing concentrations of test compounds or standard were incubated with membrane receptors and radioligand in 5 mM $MgCl_2$ and 50 mM TRIS-HCl (pH 7.4) for 60 minutes at room temperature. The reaction was terminated by rapid vacuum filtration onto the glass fiber filters. Radioactivity trapped onto the filters was determined and compared to the control values in order to ascertain any interactions of the test compound(s) with either cloned human or rat receptor binding site.
Results:

| S. No | Example | Human histamie-3 receptor $K_i$ (nM) | Rat histamine-3 receptor $K_i$ (nM) |
|---|---|---|---|
| 1 | Compound 1 | 8.7 | 9.8 |
| 2 | Compound 2 | 19.9 | ND |
| 3 | Compound 3 | 8.3 | ND |

ND—Not done

Reference:
Br J Pharmacol., 2008, 154(6): 1166-1181.

Example 2

Determination of $IC_{50}$ Values at Histamine-3 Receptor

Test compounds were evaluated according to the following procedures to determine the $IC_{50}$ values.
Materials and Methods:
Receptor source: Human recombinant (CHO-K1 cells)
Radioligand: [35S]-GTPγS
Final ligand concentration: [0.3 nM]
Reference compound: Thioperamide
Positive control: Thioperamide
Incubation Conditions:

Increasing concentrations of test compounds and/or vehicle is pre-incubated with the membranes (0.09 mg/mL) and 10 µM GDP in modified HEPES pH 7.4 buffer (20 mM HEPES, pH 7.4, 100 mM NaCl, 10 mM $MgCl_2$, 1 mM DTT, 1 mM EDTA) for 20 minutes and SPA beads are then added for another 60 minutes at 30° C. The reaction is initiated by 0.3 nM [$^{35}$S]GTPγS for an additional 30 minutes incubation period. Test compound-induced increase of [$^{35}$S]GTPγS binding by 50 percent or more (≥50%) relative to the 3 µM R(-)-a-methylhistamine response indicates possible histamine-3 receptor agonist activity. Test compound induced inhibition of 0.03 µM R(-)-a-methylhistamine-induced increase of [$^{35}$S]GTPγS binding response by 50 percent or more (≥50%) indicates receptor antagonist activity. These studies were conducted and the data were analyzed at Eurofins Panlabs Taiwan Ltd, Taiwan using standard radioligand binding techniques as described above.
Results:
Compound 1 exhibits inverse agonist like properties in GTPγS assay on human recombinant histamine-3 receptor with $IC_{50}$ value of 20 nM.
Reference:
J. Neurochem., 1998, 71(2): 808-816.

Example 3

Object Recognition Task Model

The cognition enhancing properties of compounds of this invention were estimated by using this model.

Male Wistar rats (8-10 weeks old) were used as experimental animals. Four animals were housed in each cage. Animals were kept on 20% food deprivation from a day prior to experimentation. Water was provided ad libitum throughout the experiment. Animals were maintained on a 12 hours light/dark cycle in temperature and humidity controlled room. The experiment was carried out in an open field made up of acrylic. Rats were habituated to individual arenas (open field) in the absence of any objects on day 1.

Rats received vehicle, donepezil or test compound and AChEI (donepezil, galantamine or rivastigmine) on the day of habituation, before familiar ($T_1$) and choice ($T_2$) trials. During the familiarization phase ($T_1$), the rats were placed individually in the arena for 3 minutes, in which two identical objects ($a_1$ and $a_2$) were positioned 10 cm from the wall. 24 hours after $T_1$, trial for long-term memory test was assessed. The same rats were placed in the same arena as they were placed in $T_1$ trial. During the choice phase ($T_2$) rats were allowed to explore the arena for 3 minutes in presence of a copy of familiar object ($a_3$) and one novel object (b). During the $T_1$ and $T_2$ trial, explorations of each object (defined as sniffing, licking, chewing or having moving vibrissae whilst directing the nose towards the object at a distance of less than 1 cm) were recorded using stopwatch.

$T_1$ is the total time spent exploring the familiar objects ($a_1+a_2$).

$T_2$ is the total time spent exploring the familiar object and novel object ($a_3+b$).

The object recognition test was performed as described in *Behavioural Brain Research*, 1988, 31, 47-59.

Results:

Vehicle or test compound or AChEI treated animals spent almost equal time exploring the novel and the familiar objects. The groups treated with combination of test compound and AChEI (donepezil, galantamine or rivastigmine) spent significantly more time exploring the novel object and discriminated between the novel and familiar object. This procognitive effect suggests a potentiating effect of test compound over the procognitive effect of AChEI (donepezil, galantamine or rivastigmine) alone. The results of this study are provided in FIG. 1a, 1b, 1c and 2.

Example 4

Evaluation of Acetylcholine Modulation in Medial Prefrontal Cortex of Male Wistar Rats Male Wistar rats (240-300 g body weight) were stereotaxically implanted with a microdialysis guide cannula in medial prefrontal cortex (mPFC; AP: +3.2 mm, ML: −0.5 mm, DV: −3.0 mm) under isoflurane anesthesia. Co-ordinates were taken according to atlas for the rat brain (Paxinos and Watson 2004) with reference points taken from bregma and vertical from the skull. The rats were allowed to recover individually for four days in a round bottom Plexiglas bowl with free access to feed and water.

After surgical recovery of 4 days, male Wistar rats were connected to dual quartz lined two-channel liquid swivel (Instech, UK) on a counter balance lever arm, which allowed unrestricted movements of the animal. Sixteen hours before start of the study, a pre-equilibrated microdialysis probe (2 mm dialysis membrane) was inserted into mPFC through the guide cannula. On the day of study, probe was perfused with artificial cerebrospinal fluid (aCSF; NaCl 147 mM, KCl 2.7 mM, $MgCl_2$ 1 mM, $CaCl_2 \cdot 2H_2O$ 1.2 mM, pH 7.4) at a flow rate of 1.5 μL/min and a stabilization period of 2 h was maintained. Five basal samples were collected at 20 min intervals prior to the treatment of test Compounds (3 or 10 mg/kg, p.o.) or vehicle. Donepezil (1 mg/kg, s.c.) or rivastigmine (0.5 mg/kg, s.c.) was administered 30 min after administration of test compounds. Dialysate samples were collected for an additional period of 4 h post treatment of test compounds. Dialysates were stored below −50° C. prior to analysis.

Quantitation of Acetylcholine

Acetylcholine concentrations in dialysates were quantified using LC-MS/MS based method.

Statistical Analysis:

All microdialysis data for acetylcholine was plotted as percent change from mean dialysate basal concentrations with 100% defined as the average of five pre-dose values. The percent change in acetylcholine levels after combination treatment were compared with donepezil or rivastigmine using two-way analysis of variance (time and treatment), followed by Bonferroni's posttest. Area under the curve (AUC) values for percent change in acetylcholine levels were calculated and the statistical significance between the mean AUC value after combination treatment was compared against AUC values after donepezil or rivastigmine treatment alone using unpaired "t" test. Statistical significance was considered at a p value less than 0.05. Incorrect probe placement was considered as criteria to reject the data from animal.

Reference:
1. Paxinos G. and Watson C. (2004) Rat brain in stereotaxic coordinates. Academic Press, New York.

Results:

Compound 1

Figure 1A:
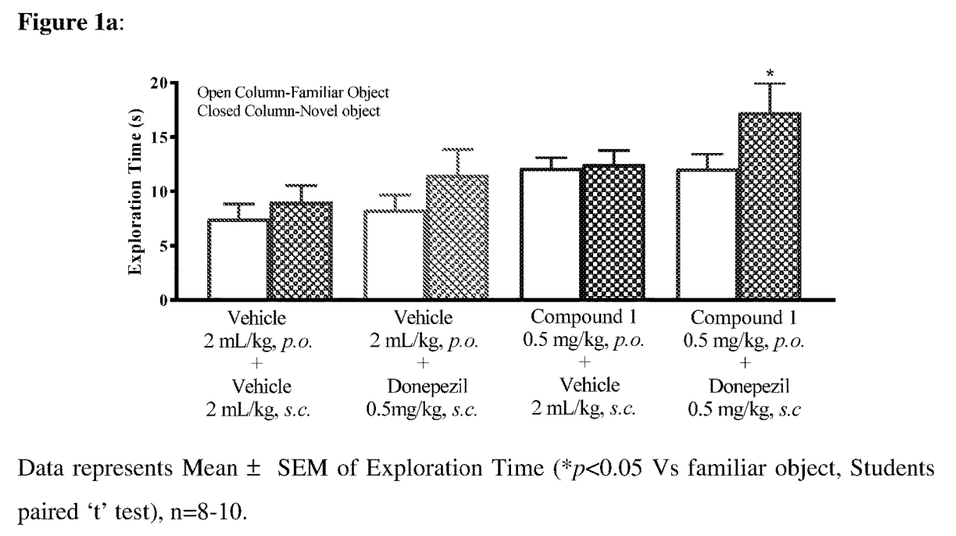
FIG. 1a depicts the results of the effect of a co-treatment of compound 1 with donepezil on cognition enhancing properties using object recognition task model.
Figure 1B:
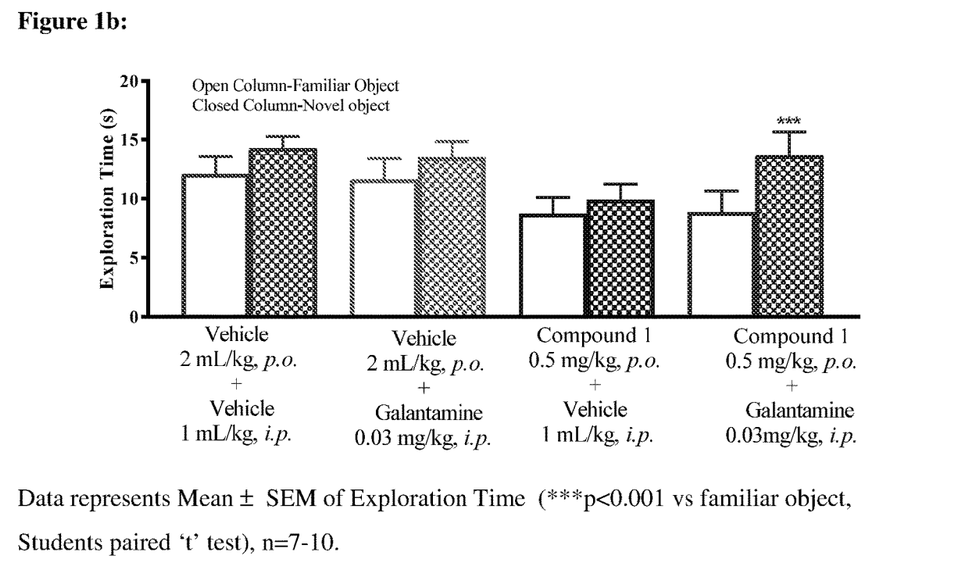
FIG. 1b depicts the results of the effect of a co-treatment of compound 1 with galantamine on cognition enhancing properties using object recognition task model.
Figure 1C:
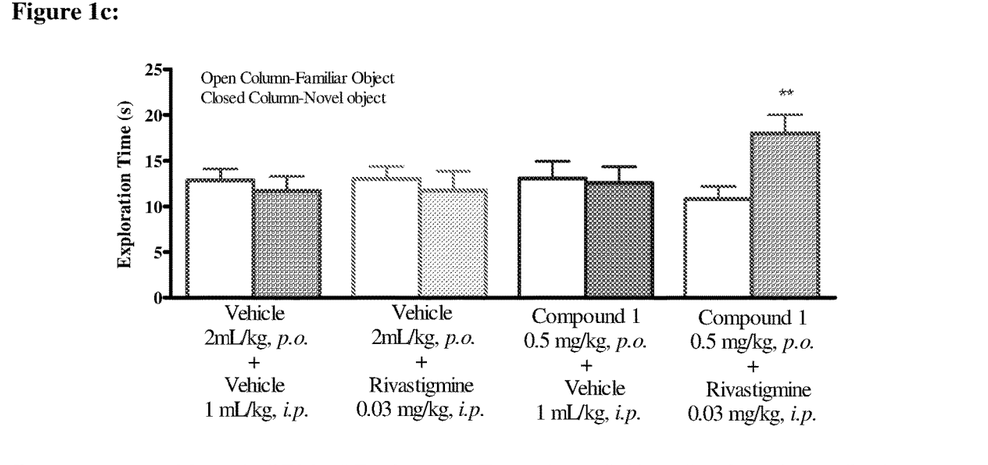
FIG. 1c depicts the results of the effect of a co-treatment of compound 1 with rivastigmine on cognition enhancing properties using object recognition task model.
Figure 2:
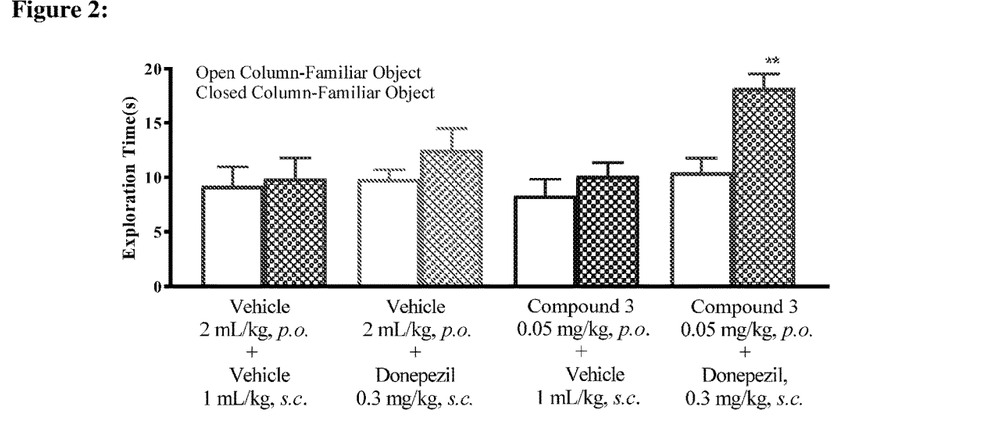
FIG. 2 depicts the results of the effect of a co-treatment of compound 3 with donepezil on cognition enhancing properties using object recognition task model.
Figure 3:
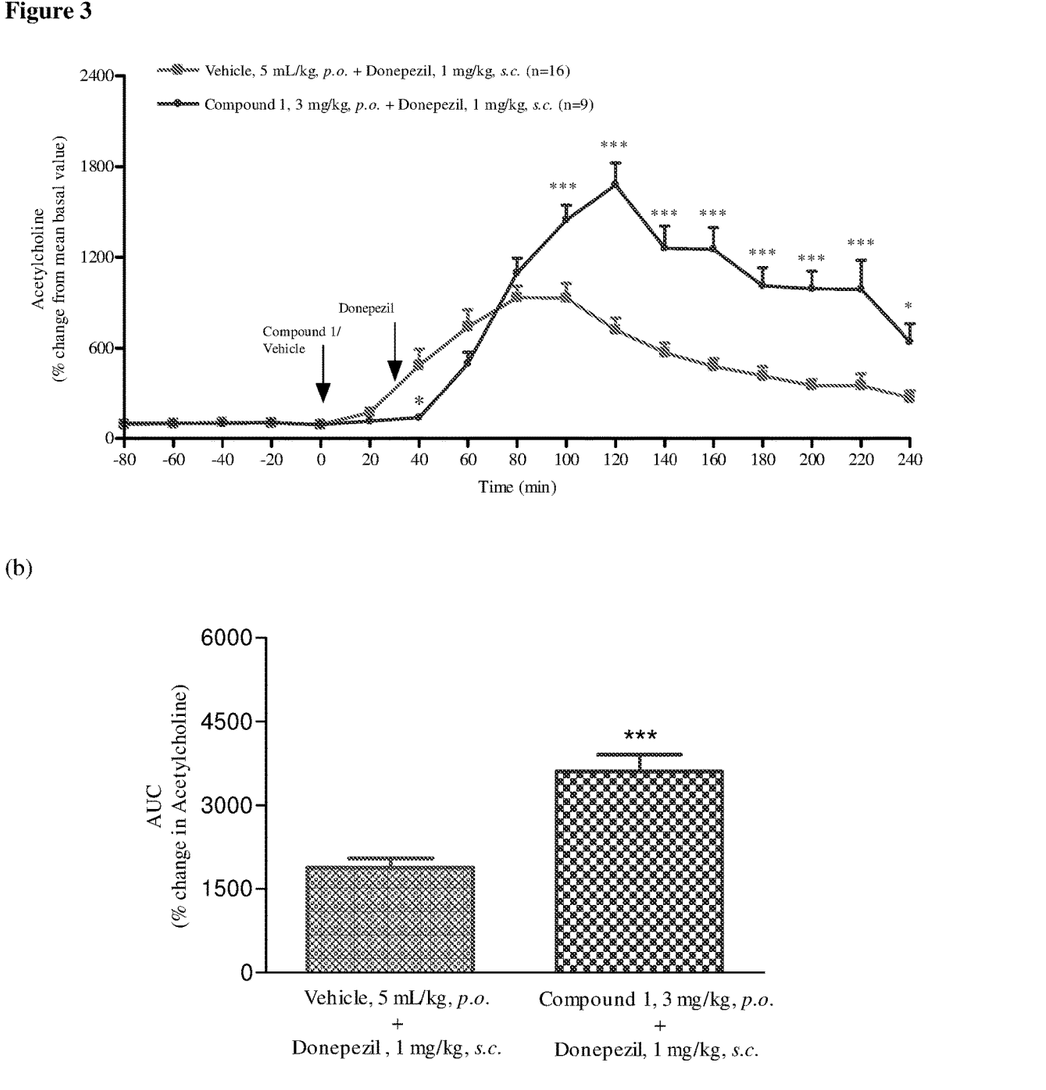
FIG. 3 depicts the effect of compound 1 in combination with donepezil on extracellular levels of acetylcholine in medial prefrontal cortex of male Wistar rats.

Treatment with donepezil produced increase in baseline cortical acetylcholine levels and reached to the maximum of 933±74% of basal levels. Compound 1 in combination with donepezil produced significant increase in acetylcholine levels and peak levels reached up to 1676±150% of pre-dose levels (FIG. 3(a)). Mean area under the curve values (AUC) calculated after combination treatment of Compound 1 and donepezil were significantly higher compared to donepezil alone (FIG. 3(b)).

Figure 4:
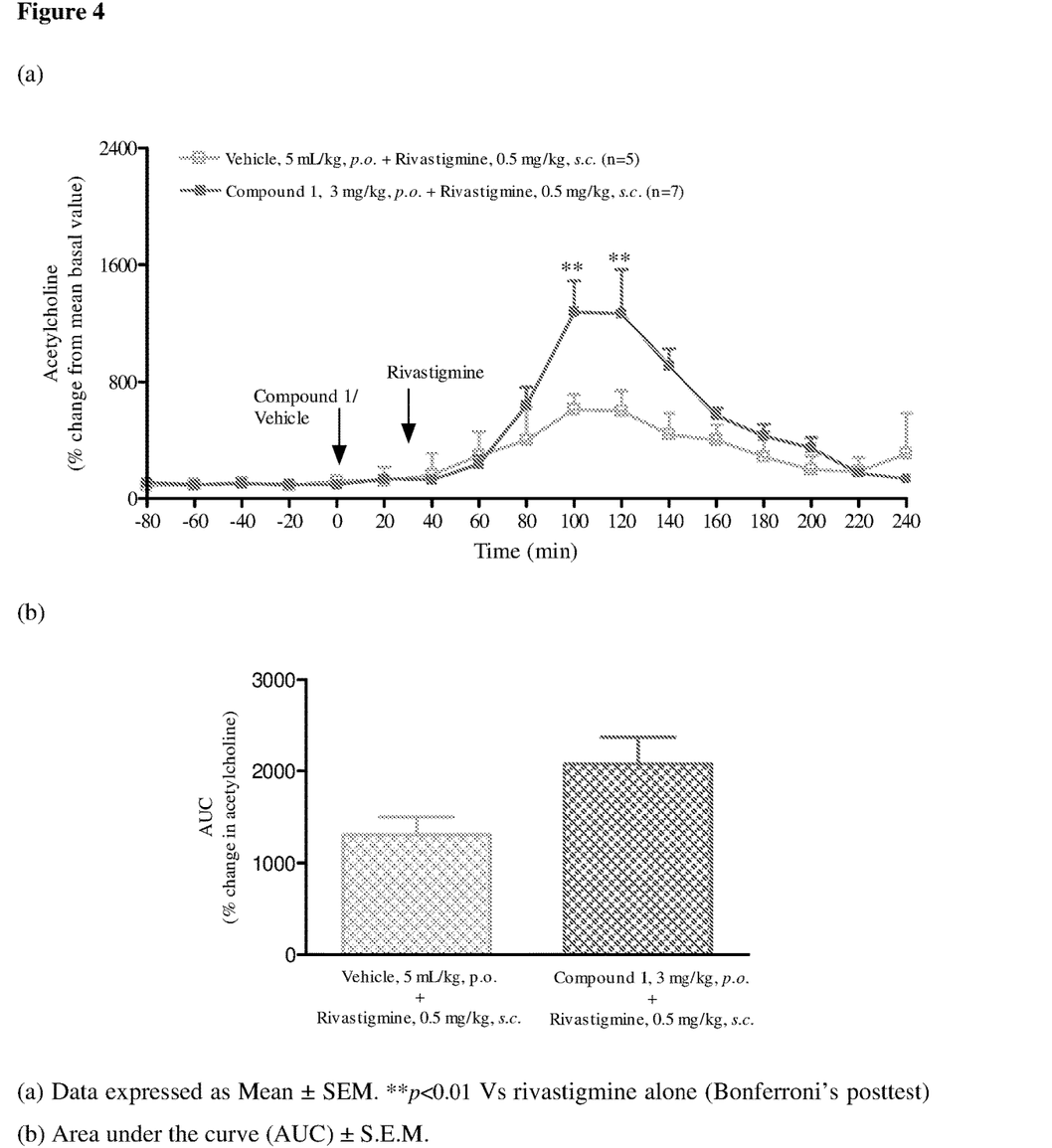
FIG. 4 depicts the effect of compound 1 in combination with rivastigmine on extracellular levels of acetylcholine in medial prefrontal cortex of male Wistar rats.

Treatment with rivastigmine produced increase in baseline cortical acetylcholine levels and reached to the maximum of 612±104% of basal levels. Compound 1 in combination with rivastigmine produced significant increase in acetylcholine levels and peak levels reached up to 1276±213% of pre-dose levels (FIG. 4(a)). Mean area under the curve values (AUC) calculated after combination treatment of Compound 1 and rivastigmine were higher compared to rivastigmine alone (FIG. 4(b)).

Compound 2

Figure 5:
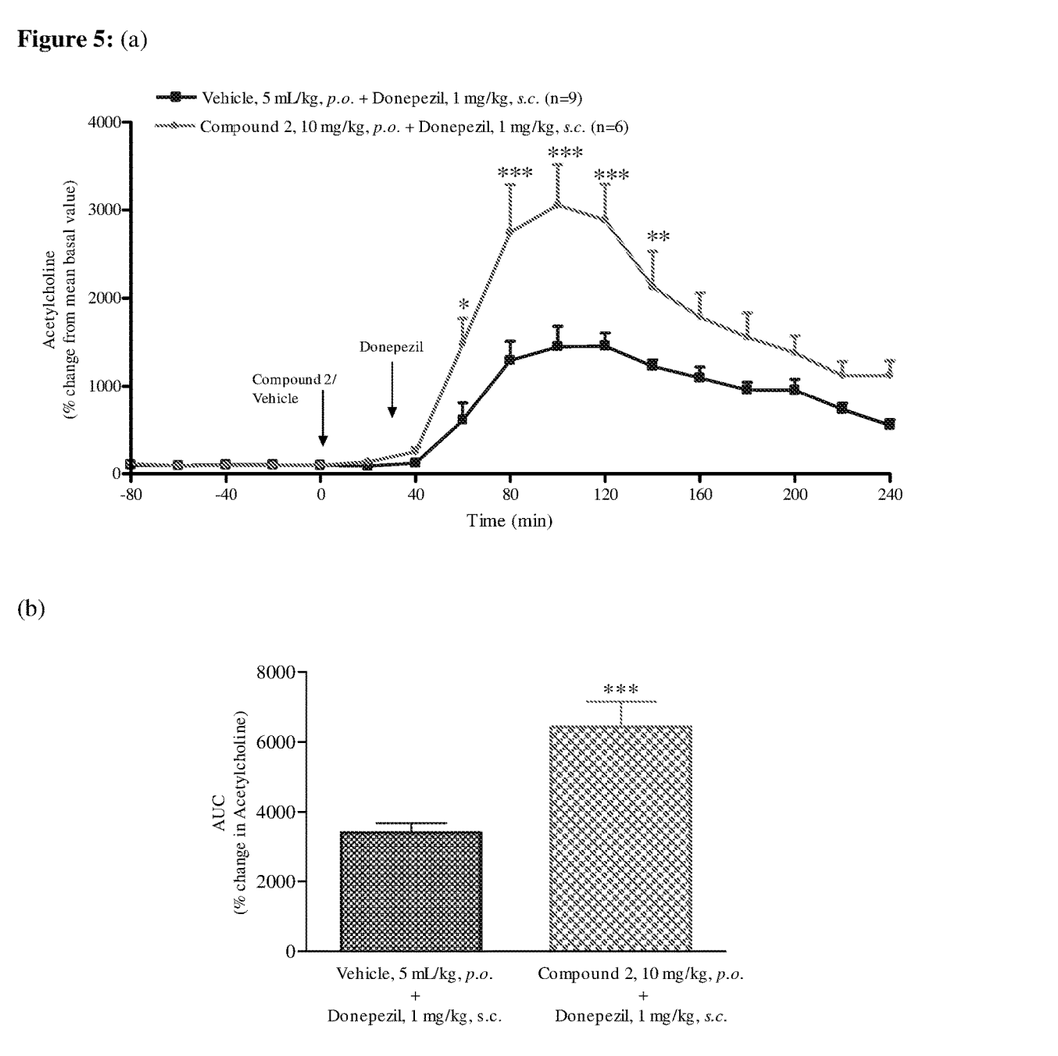
FIG. 5 depicts the effect of compound 2 in combination with donepezil on extracellular levels of acetylcholine in medial prefrontal cortex of male Wistar rats.

Treatment with donepezil produced increase in baseline cortical acetylcholine levels and reached to the maximum of 1459±146% of basal levels. Compound 2 in combination with donepezil produced significant increase in acetylcholine levels and peak levels reached up to 3057±468% of pre-dose levels (FIG. 5(a)). Mean area under the curve values (AUC) calculated after combination treatment of Compound 2 and Donepezil were significantly higher compared to Donepezil alone (FIG. 5b).

Compound 3

Figure 6:
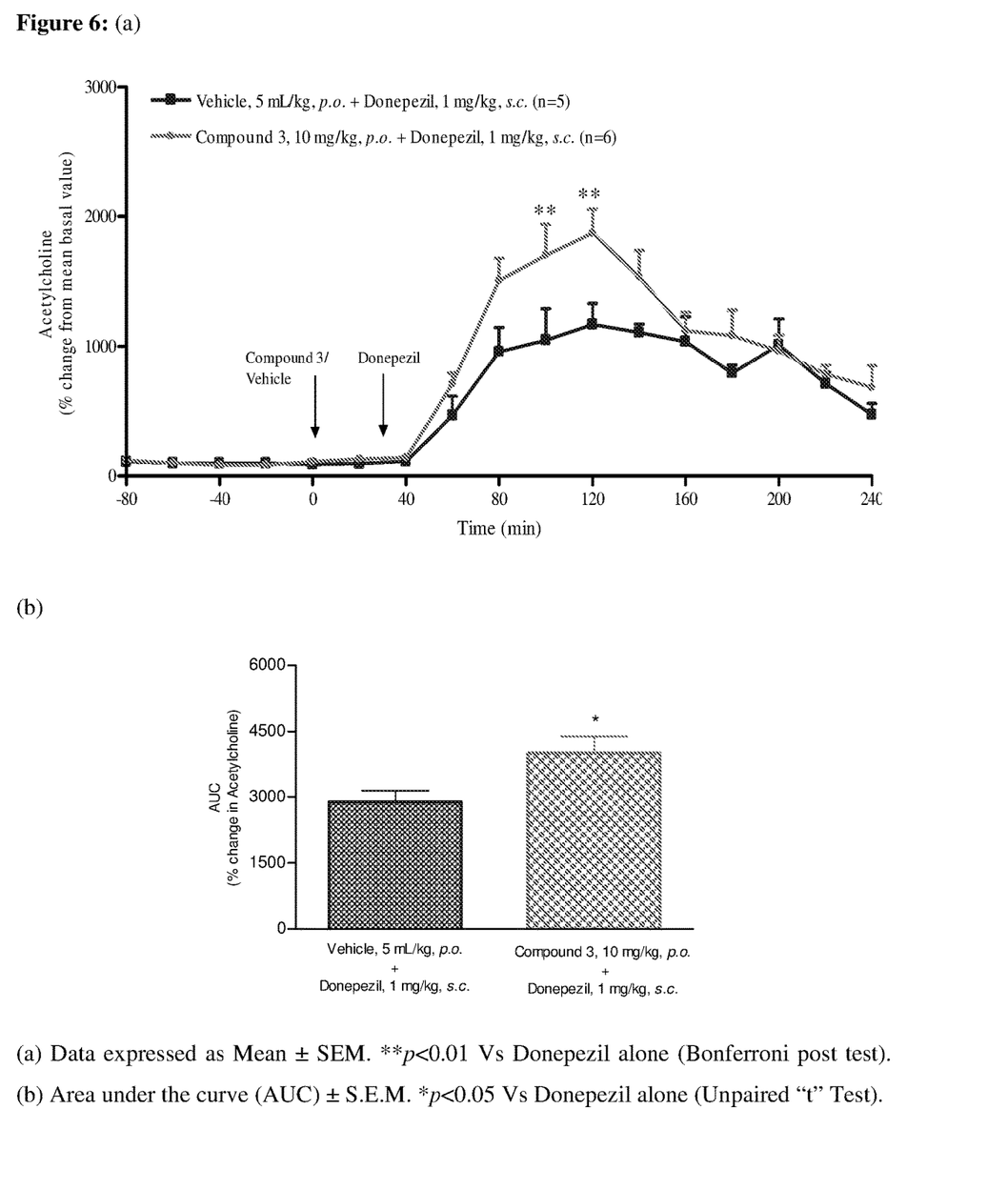
FIG. 6 depicts the effect of compound 3 in combination with donepezil on extracellular levels of acetylcholine in medial prefrontal cortex of male Wistar rats.

Treatment with donepezil produced increase in baseline cortical acetylcholine levels and reached to the maximum of 1170±161% of basal levels. Compound 3 in combination with donepezil produced significant increase in acetylcholine levels and peak levels reached up to 1874±184% of pre-dose levels (FIG. 6(a)). Mean area under the curve values (AUC) calculated after combination treatment of Compound 3 and donepezil were significantly higher compared to donepezil alone (FIG. 6(b)).

Example 5

Evaluation of Theta Modulation in Dorsal Hippocampus of Anesthetized Male Wistar Rats Male Wistar rats (240-320 g) were anesthetized by intraperitoneal administration of urethane (1.2 to 1.5 g/kg) for implantation of a catheter in the left femoral vein. The animal was placed in a stereotaxic frame for implanting an electrode (stainless steel wire, Plastics One) into the dorsal hippocampus (AP, −3.8 mm; ML, +2.2 mm; DV, −2.5 mm; Paxinos and Watson, 2004). Bipolar stimulating electrode (untwisted stainless steel wires, separated by 0.75-1.0 mm at their tips, Plastics One) was implanted in the Nucleus Pontis Oralis (NPO; AP, −7.8 mm; ML, 1.8 mm; DV, −6.0 mm; Paxinos and Watson, 2004). Additionally one electrode was implanted into the cerebellum which served as a reference. Hippocampal θ rhythm was evoked via a 6-s electrical stimulation train (20-160 µA, 0.3-ms pulse duration, 250 Hz) delivered to the NPO at a rate of 0.01 trains/s with a Grass S88 stimulator and PSIU6 stimulus isolation unit (Grass Medical Instruments, Quincy, Mass.). EEG was recorded at a rate of 1000 Hz using Ponemah (Version 5.2) software and stored for off-line analysis using NeuroScore (Version 3.0). Baseline amplitude level was achieved by using the current required to elicit θ rhythm to 50% of the maximal amplitude under control conditions. After the stabilization period of one hour, baseline recording was done for 30 min followed by the treatment of vehicle or Compound 1 (1 mg/kg, i.v.). Donepezil (0.3 mg/kg, i.v.) was administered 30 min after Compound 1 treatment and recording was continued for additional 1 hour.

Statistical Analysis:

Power in the θ rhythm frequency in the stimulation period during the 30-min baseline period was calculated and the % changes in these measures post treatment were calculated. The percent change in relative theta power after combination treatment was compared with donepezil using two-way analysis of variance (time and treatment), followed by Bonferroni's posttest. Statistical significance was considered at a p value less than 0.05.

Figure 7:
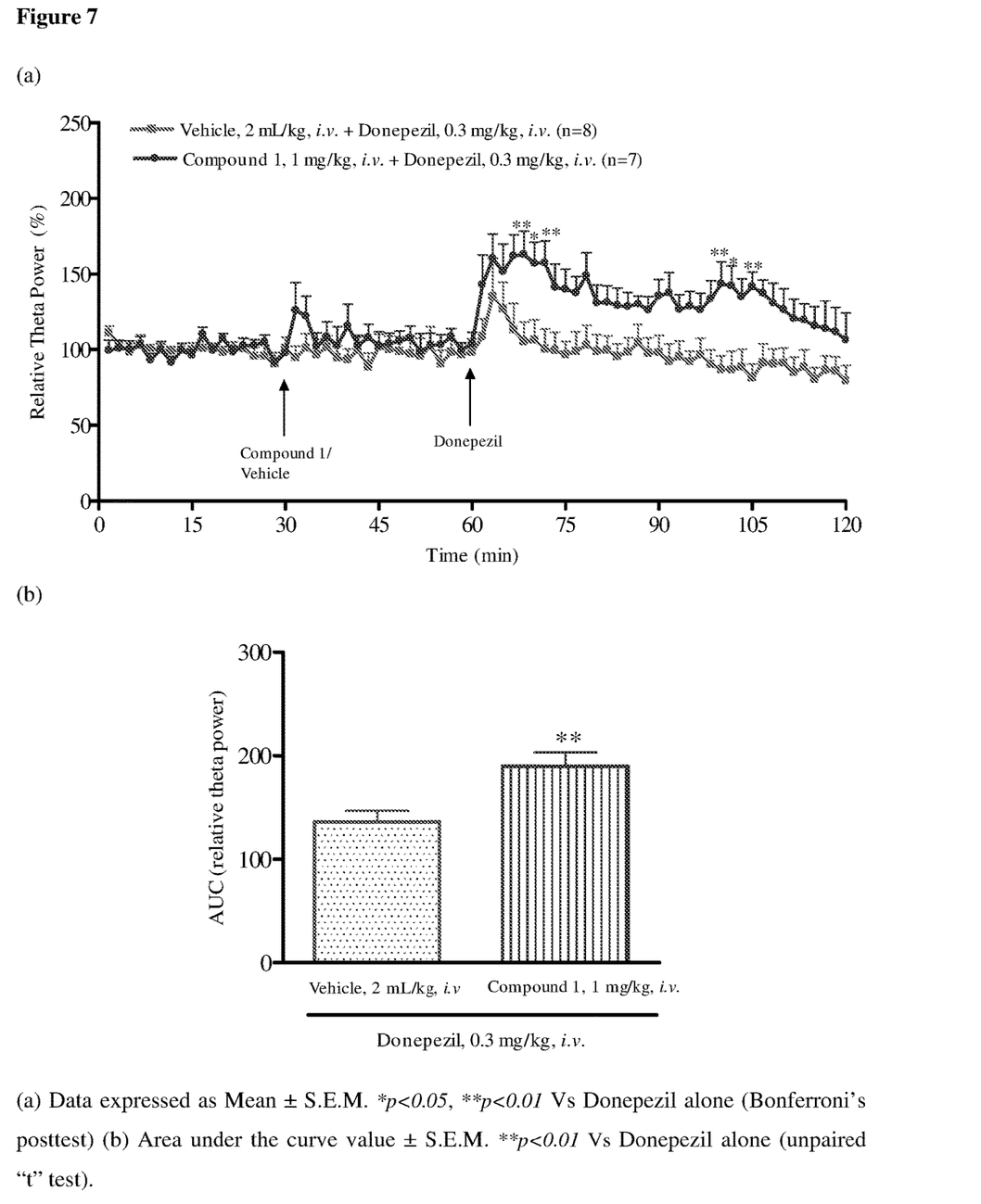
FIG. 7 depicts the results of the effect of compound 1 and donepezil combination on stimulation evoked theta levels in dorsal hippocampus of anesthetized male Wistar rats.

Reference:
1. Paxinos G. and Watson C. (2004) Rat brain in stereotaxic coordinates. Academic Press, New York Results:

Treatment with donepezil produced increase in hippocampal theta power. Compound 1 in combination with donepezil produced significant increase in theta power levels and peak levels reached up to 163±15% of pre-dose levels (FIG. 7(a)). Mean area under the curve values (AUC) calculated after the treatment of compound 1 and donepezil were significantly higher compared to donepezil (FIG. 7(b)).

We claim:
1. A combination comprising a histamine-3 receptor inverse agonist and an acetylcholinesterase inhibitor; wherein the histamine-3 receptor inverse agonist is selected from the group consisting of:
N-[4-(1-Cyclobutylpiperidin-4-yloxy)phenyl]-2-(morpholin-4-yl)acetamide;
N-[4-(1-Cyclopropylpiperidin-4-yloxy)phenyl]2-(morpholin-4-yl)acetamide; and
N-[4-(1-lsopropylpiperidin-4-yloxy)phenyl]-2-(morpholin-4-yl)acetamide;
or a pharmaceutically acceptable salt thereof, wherein the acetylcholinesterase inhibitor is selected from the group consisting of donepezil, rivastigmine and galantamine or a pharmaceutically acceptable salt thereof.

2. The combination as claimed in claim 1, wherein the histamine-3 receptor inverse agonist is N-[4-(1-Cyclobutylpiperidin-4-yloxy)phenyl]-2-(morpholin-4-yl)acetamide or a pharmaceutically acceptable salt thereof.

3. The combination as claimed in claim 1, wherein the pharmaceutically acceptable salt of the histamine-3 receptor inverse agonist is,
N-[4-(1-Cyclobutylpiperidin-4-yloxy)phenyl]-2-(morpholin-4-yl)acetamide dihydrochloride;
N-[4-(1-Cyclopropylpiperidin-4-yloxy)phenyl]-2-(morpholin-4-yl)acetamide tartrate; and
N-[4-(1-lsopropylpiperidin-4-yloxy)phenyl]-2-(morpholin-4-yl)acetamide tartrate.

4. The combination as claimed in claim 1, wherein histamine-3 receptor inverse agonist is N-[4-(1-Cyclobutylpiperidin-4-yloxy)phenyl]-2-(morpholin-4-yl)acetamide dihydrochloride.

5. The combination as claimed in claim 1, wherein the acetylcholinesterase inhibitor is donepezil or a pharmaceutically acceptable salt thereof.

6. The combination as claimed in claim 5, wherein the acetylcholinesterase inhibitor is donepezil hydrochloride.

7. A combination comprising N-[4-(1-Cyclobutylpiperidin-4-yloxy)phenyl]-2-(morpholin-4-yl)acetamide dihydrochloride and donepezil hydrochloride.

8. The combination as claimed in claim 1 or claim 7, for the treatment of cognitive disorders in a patient.

9. The combination as claimed in claim 8, wherein the cognitive disorder is selected from Alzheimer's disease, schizophrenia, Parkinson's disease, Lewy body dementia, vascular dementia, frontotemporal dementia, Down syndrome and Tourette's syndrome.

10. A pharmaceutical composition comprising the combination as claimed in claim 1 or claim 7, and pharmaceutically acceptable excipients or combination thereof.

11. The pharmaceutical composition as claimed in claim 10, for the treatment of cognitive disorders selected from Alzheimer's disease, schizophrenia, Parkinson's disease, Lewy body dementia, vascular dementia and frontotemporal dementia.

12. The pharmaceutical composition as claimed in claim 10, wherein the N-[4-(1-Cyclobutylpiperidin-4-yloxy)phenyl]-2-(morpholin-4-yl)acetamide or a pharmaceutically acceptable salt thereof is present in an amount of 0.1 mg to 100 mg.

13. The pharmaceutical composition as claimed in claim 10, wherein the N-[4-(1-Cyclobutylpiperidin-4-yloxy)phenyl]-2-(morpholin-4-yl)acetamide or a pharmaceutically acceptable salt thereof is present in an amount of 0.1 mg to 60 mg.

14. The pharmaceutical composition as claimed in claim 10, wherein the N-[4-(1-Cyclobutylpiperidin-4-yloxy)phenyl]-2-(morpholin-4-yl)acetamide or a pharmaceutically acceptable salt thereof is present in an amount of 0.1 mg to 30 mg.

15. The pharmaceutical composition as claimed in claim 10, wherein the donepezil or a pharmaceutically acceptable salt thereof is present in an amount of 2 mg to 30 mg.

16. A method of treatment of cognitive disorders comprising the step of administering to a patient in need thereof, a therapeutically effective amount of the combination as claimed in claim 1 or claim 7.

17. The method of treatment as claimed in claim 16, wherein the cognitive disorder is selected from Alzheimer's disease, schizophrenia, Parkinson's disease, Lewy body dementia, vascular dementia, frontotemporal dementia, Down syndrome and Tourette's syndrome.

18. A method of treating Alzheimer's disease in a patient comprising the step of administering to said patient a therapeutically effective amount of N-[4-(1-Cyclobutylpiperidin-4-yloxy)phenyl]-2-(morpholin-4-yl)acetamide or a pharmaceutically acceptable salt thereof and acetylcholinesterase inhibitor, wherein the acetylcholinesterase inhibitor is donepezil, rivastiqmine and qalantamine or a pharmaceutically acceptable salt thereof.

19. A method of treating Alzheimer's disease in a patient on stable treatment with acetylcholinesterase inhibitor comprising the step of administering to said patient a therapeutically effective amount of N-[4-(1-Cyclobutylpiperidin-4-yloxy)phenyl]-2-(morpholin-4-yl)acetamide or a pharmaceutically acceptable salt thereof, wherein the acetylcholinesterase inhibitor is donepezil, rivastigmine and galantamine or a pharmaceutically acceptable salt thereof.

20. The method of treating Alzheimer's disease as claimed in claim 18 or claim 19, wherein the pharmaceutically acceptable salt of N-[4-(1-Cyclobutylpiperidin-4-yloxy)phenyl]-2-(morpholin-4-yl)acetamide is N-[4-(1-Cyclobutylpiperidin-4-yloxy)phenyl]-2-(morpholin-4-yl)acetamide dihydrochloride.

21. The method of treating Alzheimer's disease as claimed in claim 18 or claim 19, wherein the patient is administered 0.1 mg to 100 mg of N-[4-(1-Cyclobutylpiperidin-4-yloxy)phenyl]-2-(morpholin-4-yl)acetamide or a pharmaceutically acceptable salt thereof per day.

22. The method of treating Alzheimer's disease as claimed in claim 18 or claim 19, wherein the patient is administered 0.1 mg to 60 mg of N-[4-(1-Cyclobutylpiperidin-4-yloxy)phenyl]-2-(morpholin-4-yl)acetamide or a pharmaceutically acceptable salt thereof per day.

23. The method of treating Alzheimer's disease as claimed in claim 18 or claim 19, wherein the patient is administered 0.1 mg to 30 mg of N-[4-(1-Cyclobutylpiperidin-4-yloxy)phenyl]-2-(morpholin-4-yl)acetamide or a pharmaceutically acceptable salt thereof per day.

24. The method of treating Alzheimer's disease as claimed in claim 18 or claim 19, wherein the patient is administered 1 mg to 30 mg of donepezil, or a pharmaceutically acceptable salt thereof per day.

25. The method of treating Alzheimer's disease as claimed in claim 18, wherein the N-[4-(1-Cyclobutylpiperidin-4-yloxy)phenyl]-2-(morpholin-4-yl)acetamide or a pharmaceutically acceptable salt thereof is administered to the patient by oral, nasal, local, dermal or parenteral routes.

26. The method of treating Alzheimer's disease as claimed in claim 18, wherein the N-[4-(1-Cyclobutylpiperidin-4-yloxy)phenyl]-2-(morpholin-4-yl)acetamide or a pharmaceutically acceptable salt thereof is administered to the patient one to three times per day, one to three times per week or one to three times per month.

\* \* \* \* \*